United States Patent [19]
Cook

[11] Patent Number: 5,985,951
[45] Date of Patent: Nov. 16, 1999

[54] UV-CURABLE NAIL COATING FORMULATIONS CONTAINING CELLULOSE ESTERS WITH ETHYLENICALLY UNSATURATED PENDANT GROUPS

[75] Inventor: Phillip Michael Cook, Kingsport, Tenn.

[73] Assignee: Eastman Chemical Company, Kingsport, Tenn.

[21] Appl. No.: 09/069,353

[22] Filed: Apr. 29, 1998

Related U.S. Application Data

[60] Provisional application No. 60/045,285, May 1, 1997.

[51] Int. Cl.$^6$ ............... C09K 101/02; C08F 2/46
[52] U.S. Cl. ............... 522/88; 522/86; 522/89; 536/76; 424/401; 424/61
[58] Field of Search ............ 424/61, 401; 522/88, 522/89, 86, 81; 156/344; 536/76, 69; 427/514, 517

[56] References Cited

U.S. PATENT DOCUMENTS

| | | |
|---|---|---|
| 3,483,289 | 12/1969 | Michaelson et al. . |
| 3,896,014 | 7/1975 | Rosenberg . |
| 4,058,442 | 11/1977 | Lee, Jr. et al. . |
| 4,134,809 | 1/1979 | Pacifici et al. ............ 204/159.12 |
| 4,147,603 | 4/1979 | Pacifici et al. ............ 204/159.12 |
| 4,409,203 | 10/1983 | Gordon et al. . |
| 4,565,857 | 1/1986 | Grant ............ 527/301 |
| 4,656,202 | 4/1987 | Nason et al. ............ 522/89 |
| 4,682,612 | 7/1987 | Giuliano . |
| 4,704,303 | 11/1987 | Cornell . |
| 4,712,571 | 12/1987 | Remz et al. . |
| 4,749,564 | 6/1988 | Faryniarz et al. . |
| 4,749,773 | 6/1988 | Weaver et al. . |
| 4,826,903 | 5/1989 | Weaver et al. . |
| 4,839,230 | 6/1989 | Cook . |
| 4,845,188 | 7/1989 | Weaver et al. . |
| 4,855,184 | 8/1989 | Klun et al. ............ 428/425.1 |
| 4,882,412 | 11/1989 | Weaver et al. . |
| 4,892,922 | 1/1990 | Weaver et al. . |
| 4,892,923 | 1/1990 | Weaver et al. . |
| 5,109,097 | 4/1992 | Klun et al. . |
| 5,130,125 | 7/1992 | Martin et al. . |
| 5,138,006 | 8/1992 | Cook et al. ............ 527/301 |
| 5,254,429 | 10/1993 | Gracia et al. . |
| 5,407,666 | 4/1995 | Patel et al. . |
| 5,424,061 | 6/1995 | Pappas et al. . |
| 5,512,273 | 4/1996 | Martin . |
| 5,516,509 | 5/1996 | Marr-Leisy et al. . |
| 5,741,901 | 4/1998 | Cook et al. ............ 536/76 |

FOREIGN PATENT DOCUMENTS

WO 97/18242  5/1997  WIPO .

*Primary Examiner*—James J. Seidleck
*Assistant Examiner*—Sanza McClendon
*Attorney, Agent, or Firm*—Jonathan D. Wood; Betty J. Boshears; Harry J. Gwinnell

[57] ABSTRACT

This invention relates to a composition of photopolymerizable coatings forming cosmetic films that are especially useful for human and animal nail coatings. The coating compositions are based on certain cellulose ester derivatives, which possess groups capable of free radical addition reactions with unsaturated ethylenic pendant groups on other compounds upon exposure to actinic radiation in the presence of an photoinitiator. The coating compositions contain solvents, pigments, modifying resins, plasticizers, and other compounds mixed and maintained in a liquid solution.

38 Claims, No Drawings

UV-CURABLE NAIL COATING FORMULATIONS CONTAINING CELLULOSE ESTERS WITH ETHYLENICALLY UNSATURATED PENDANT GROUPS

REFERENCE TO RELATED APPLICATION

This application claims the benefit of U.S. Provisional Application No. 60/045,285 filed on May 1, 1997.

FIELD OF THE INVENTION

This invention relates generally to compositions of photopolymerizable cosmetic film forming coatings that are especially useful for human nail coatings. The compositions are based on certain cellulose ester derivatives, which possess groups capable of free radical additional reactions with ethylenic groups on other compounds upon exposure to actinic radiation in the presence of an initiator. After deposition on the nail, the films of such compositions are substantially hardened and toughened on exposure to actinic radiation.

BACKGROUND OF THE INVENTION

Cellulose esters are used extensively in lacquer coatings, such as nail polishes, because they are compatible with many resins, solvents, and additives, they exhibit good gap-filling properties, they dry quickly, they exhibit low toxicity, and they form a very aesthetically-pleasing coating on a variety of substrates. Nail polishes include thermoplastic coatings which harden after application by the evaporation of the solvents contained in the polishes. The thermoplastic coatings have contained cellulose esters, resins, solvents, pigments and other additives. Because thermoplastic nail polishes are soft and easily scratched, they are often modified or "hardened" by addition of formaldehyde-based resins, as described in U.S. Pat. Nos. 5,424,061 (Pappas et al.), U.S. Pat. No. 4,749,564 (Faryniarz), and U.S. Pat. No. 4,712,571 (Renz et al.). Such resins can cause hardening of the nail coating to the point of film embrittlement and can even lead to release of formaldehyde, which can react with the nail surface. Many nail polishes use nitrocellulose as the major film former as described in U.S. Pat. Nos. 5,424,061 (Pappas et al.) and U.S. Pat. No. 4,749,564 (Faryniarz et al.). Nitrocellulose is well-known for its tendency to become embrittled and yellow over time, and even lead to staining or yellowing of the nails. Because of its flammability, nitrocellulose requires special storage and handling. Such disadvantages have served to prompt a search for suitable substitutes.

Because of their clarity, compatibility with many resins and solvents, gap filling properties, pigment wetting properties, and rapid solvent release, cellulose acetate, cellulose acetate butyrate, cellulose acetate propionate, and mixtures thereof may be substituted for nitrocellulose. Such is described in U.S. Pat. Nos. 3,483,289 (Michaelson et al.), U.S. Pat. No. 4,409,203 (Gordon et al.), U.S. Pat. No. 4,712,571 (Remz et al.), U.S. Pat. No. 5,130,125 (Martin), U.S. Pat. No. 5,424,061 (Pappas et al.), and U.S. Pat. No. 5,512,273 (Martin). However as with other thermoplastic films, those described in said patents are prone to scratching and have essentially no solvent resistance.

Photopolymerizable nail polish formulations are described in U.S. Pat. Nos. 3,896,014 (Rosenberg), U.S. Pat. No. 4,058,442 (Lee et al.), U.S. Pat. No. 4,682,612 (Giuliano), 4,704,303 (Cornell), and U.S. Pat. No. 5,407,666 (Patel). None describe the use of photopolymerizable cellulose esters or their use in nail coating applications. Some formulations described in said patents incorporate the use of non-polymerizable cellulose esters as a viscosity modifier, but these esters are unable to participate in a crosslinking process to form a hardened, scratch resistant coating.

For the foregoing reasons, there remains a need for nail coatings that are hardened by exposure to ultraviolet light, are scratch resistant, clear in clarity after application, and non-toxic after application.

SUMMARY OF THE INVENTION

This invention relates to a photopolymerizable composition for forming a cosmetic coating useful for coating nails of humans and animals, comprising:
(a) a modified cellulose ester;
(b) a photoinitiator; and
(c) an ethylenically unsaturated crosslinking agent;
whereby upon exposure to actinic radiation the photopolymerizable composition polymerizes to form a hard and solvent resistant coating on nails; and
wherein the coating is at least partially soluble in a suitable removing solvent.

This invention further relates to a process for preparing a photopolymerizable mixture for coating surfaces comprising the steps of:
(I) mixing:
(a) a modified cellulose ester, with
(b) a photoinitiator; and
(c) a copolymerizable reactant;
in the presence of a solvent (d); and
(II) exposing the mixture in Step (I) to actinic radiation wherein the mixture polymerizes to form a hard and solvent resistant coating; and
wherein the modified cellulose ester comprises the formula:

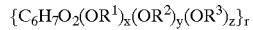

wherein (x+y+z)=3,
wherein $R^1$ is a modified cellulose ester saturated pendant group, with at least one R group independently selected from the following formulas, Acetate

Propionate

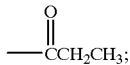

Butyrate

and

Hydroxyl, —H;

wherein $R^2$ is a modified cellulose ester ethylenically unsaturated pendant group of the formulas:

Methacrylate,

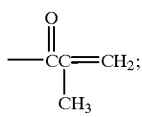

and
Acrylate,

wherein $R^3$ is a modified cellulose ester unsaturated pendant group, independantly selected from the following formulas:
Maleate/Fumarate,

m-isopropenyl-2,2-dimethylbenzyl isocyanate; and
p-isopropenyl-2,2-dimethylbenzyl isocyanate; and
wherein
x is about 0.1–2.2;
y is about 0.1–0.4;
z is about 0.1–0.6;
r is 2–250.

This invention also relates to an article comprising
(a) a substrate, and
(b) a coating thereon comprising a photopolymerized ethylenically unsaturated cellulose ester coating of the formula:

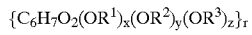

wherein: (x+y+z)=3; and
wherein $R^1$ is a modified cellulose ester saturated pendant group, with at least one R group selected from the following formulas,
Acetate,

Propionate,

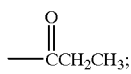

Butyrate,

and

Hydroxyl, —H;
wherein $R^2$ is a modified cellulose ester ethylenically unsaturated pendant group of the formulas:
Methacrylate,

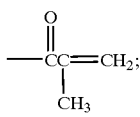

Acrylate,

wherein $R^3$ is a modified cellulose ester unsaturated pendant group, independently selected from the following formulas:
Maleate/Fumarate,

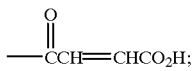

m-isopropenyl-2,2-dimethylbenzyl isocyanate; and
p-isopropenyl-2,2-dimethylbenzyl isocyanate; and
wherein
x is about 0.1–2.2;
y is about 0.1–0.4;
z is about 0.1–0.6; and
r is 50–250;
said process comprising reacting
(a) said modified cellulose ester, with
(b) a photoinitiator;
(c) a copolymerizable reactant;
(d) reactive resin;
(e) a pigment;
(f) a modifying resin; and
(g) a plasticizer;
in the presence of a co-solvent and under conditions such that the desired product is formed.

It is an object of this invention to provide a photopolymerizable cosmetic composition capable of forming a scratch resistant film useful for coating human nails.

It is a further object of this invention to provide a photopolymerizable cosmetic composition containing modified cellulose ester.

It is yet a further and more particular object of this invention to provide a photopolymerizable cosmetic composition containing a photoinitiator.

It is an additional object of this invention to provide a photopolymerizable cosmetic composition whereby upon exposure to actinic radiation, the modified cellulose ester polymerizes to form a hard durable coating on human nails.

It is a further and additional object of this invention to provide a photopolymerizable cosmetic composition whereby the hard durable coating formed can be removed with an appropriate solvent without excessive efforts.

These and other objects of the invention are accomplished by the present invention which provides for photopolymerizable nail coatings based on modified cellulose esters capable of free radical polymerization with other ethylenically unsaturated compounds when exposed to ultraviolet light in the presence of photoinitiators, pigments, solvents, modifying resins and plasticizers. Thus, the objects of the invention are accomplished by the nail coating formulations described herein.

DETAILED DESCRIPTION OF THE INVENTION

The present invention relates to cosmetic film forming polymerizable compositions utilizing cellulose esters and photoinitiators. The use of polymerizable cellulose esters to form coatings is discussed in U.S. Pat. No. 4,839,230, which is incorporated by reference herein.

The composition consists of a photopolymerizable cellulose ester, ethylenically unsaturated crosslinking agents, a solvent system, and photoinitiators. Other optional ingredients may be dyes or pigments, modifying polymers, antifoamants, opacifiers, adhesion promoters, and antioxidants.

The photopolymerizable cellulose esters useful in the present invention consist of a cellulose ester containing saturated and ethylenically unsaturated pendant groups attached to the polymer backbone of the structure:

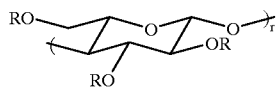

wherein r is 2 to 250; and
wherein at least one R is independently selected from the following:

|  |  | DS |
|---|---|---|
| R = Acetate | —CCH$_3$ (C=O) | 0.1–0.3 |
| Propionate | —CCH$_2$CH$_3$ (C=O) | 1.5–2.2 |
| Butyrate | —CCH$_2$CH$_2$CH$_3$ (C=O) | 1.4–2.0 |
| Hydroxyl, | —H; | 0.1–0.5 |
| Methacrylate, | —CC=CH$_2$ with CH$_3$ (C=O) | 0.1–0.4 |
| Acrylate, | —CCH=CH$_2$ (C=O) | 0.1–0.4 |
| Maleate/Fumarate, | —CCH=CHCO$_2$H (C=O) | 0.1–0.4 |
| m-isopropenyl-2,2-dimethylbenzyl isocyanate; and |  | 0.1–0.6; |
| p-isopropenyl-2,2-dimethyl benzyl isocyanate; |  | 0.1–0.6. |

The modified cellulose ester of the invention is also described by the following formula:

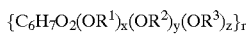

r=2 to 250, preferably 50 to 250; and
wherein (x+y+z)=3; and further wherein $R^1$, $R^2$, and $R^3$ are independently selected from the R groups as described for the structure above.

Preferably x is from about 0.1 to 2.5; y is from about 0 to 1.0; z is from about 0 to 1.0; and r is 50–250, provided that y and z are not 0 simultaneously.

Preferably y is from about 0.1 to 0.4 and z is from about 0.1 to 0.6.

It should be understood from the above structure that the group designated $C_6H_7O_2$ denotes the repeating units of alternating halves of a glucose unit, i.e., a group of the formula:

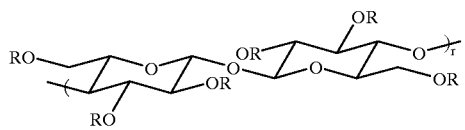

wherein r=2 to 250, preferably 50 to 250, and wherein the various R groups are as shown above.

Preferably, at least one of $R^1$, $R^2$, and $R^3$ is maleate. It is also preferable that when $R^1$, $R^2$, and $R^3$ is maleate that x=0.1 to 2.2, preferably 1.8 to 2.2, y is 0 and z is 0.1 to 0.46, preferably 0.25.

A preferred embodiment includes methacrylate and metaisopropenyl-2,2'-dimethylbenzyl isocyanate.

The cellulose ester starting materials for preparation of the modified cellulose esters may be of the acetate, propionate, or butyrate type, or mixed esters thereof. The degree of substitution per glucose ring of residual hydroxyl groups for these cellulose esters is in the range of about 0.1 to about 2.0 with about 0.3 to about 1.5 being the preferred range. Typical starting cellulose esters include, but are not limited to:

CA 320S, CA 398, CAB 381, CAB 551, CAB 553, CAP 482, CAP 504, all commercially available from Eastman Chemical Company, Kingsport, Tenn. Such cellulose ester starting materials typically have a number average molecular weight of between about 10,000 and about 75,000 Daltons as determined by gel permeation chromatography using polystyrene standards.

As used herein, the term "cellulose ester" means an unmodified cellulose ester, and the term "modified cellulose ester" means a modified cellulose ester that is a cellulose ester having at least one ethylenically unsaturated ester pendant group capable of free-radical initiated homopolymerization or co-polymerization.

Optionally, those modified cellulose esters containing pendant carboxyl groups can be rendered water dispersible by salt formation with amines if desired.

Cellulose esters generally have an inherent viscosity of about 0.2 to about 3.0 deciliters/gram as measured at a temperature of 25° C. for a 0.5 g sample in 100 ml of a 60/40 parts by weight solution of phenol/tetrachloroethane.

As a preferred aspect of the present invention, the modified cellulose esters described above are blended with co-reactive compounds which may include monomers, oligomers, or prepolymers, or polymers which possess ethylenic unsaturation and are thus capable of free-radical addition reaction with the ethylenically unsaturated pendant groups on the modified cellulose esters. Copolymerizable or co-reactive compounds such as monomers, oligomers, or prepolymers will be referred to as copolymerizable reactants, hereinafter.

Typical copolymerizable reactants (monomers) useful in the present invention include (meth)acrylic acid and their anhydrides, crotonic acid, itaconic acid and its anhydride, cyanoacrylic acid and its esters; esters of (meth)acrylic acid such as allyl, methyl, ethyl, n-propyl, isopropyl, butyl, tetrahydrofurfuryl, cyclohexyl, isobornyl, n-hexyl, n-octyl, isooctyl, 2-ethlhexyl, lauryl, stearyl, benzyl, and substituted phenoxyl, behenyl; di(meth)acrylate esters of ethylene and propylene glycols, 1,3-butylene glycols, 1,4-butanediol, diethylene and dipropylene glycols, triethylene and tripropylene glycols, 1,6-hexanediol, neopentyl glycol, polyethylene glycol; and polypropylene glycol, ethoxylated bisphenol, propoxylated neopentyl glycol; tri(meth)acrylate esters of tris-(2-hydroxethyl)isocyanurate, trimethylolpropane, pentaerythritol, glycerol, ethoxylated and propoxylated glycerol; tetra(meth)acrylate esters of pentaerythritol; acrylonitrile, vinyl acetate, vinyl toluene, styrene, N-vinyl pyrrolidinone, and alpha-methylstyrene.

Examples of blendable reactive resins (copolymerizable reactants) include epoxy (meth)acrylates, urethane (meth) acrylates, polyester (meth)acrylates, silicon (meth)acrylates, and vinyl acetates.

Typical (meth)acrylated epoxy resins would be ACTI-LANE 7220TP, ACTILANE 72, and ACTOCRYL 10020A from Anchor Chemical (UK); CRODAMER UVE series from Croda; CRAYNOR CN104 and 114 from Cray Valley; DEREKANE 200 from Dow Europe S.A.; EBECRYL 200, 220, and 3700 from Radcure Specialties; and PHOTOMER 3015 and 3016 from Henkel.

Typical silicone (meth)acrylates include EBECRYL 350 and 1360 from Radcure Specialties; PHOTOMER 7020 from Henkel; TEGO 704, 705, 725, and 726 from Goldschmidt AG; and WACKER F-737 by Wacker Silicones.

A suitable solvent i.e., suitable removing solvent and/or solvent (d), for the solvent-borne coating compositions of the present invention must be one in which the modified cellulose ester is soluble. Aliphatic hydrocarbons are generally not suitable for this purpose. Typical examples of suitable solvents include, but are not limited to ketones, alcohols, esters, chlorinated hydrocarbons, glycol ethers, glycol esters, and mixtures thereof. Specific examples include, but are not limited to acetone, 2-butanone, 2-pentanone, ethyl acetate, propyl acetate, isopropyl acetate, butyl acetate, isobutyl acetate, ethylene glycol diacetate, ethyl 3-ethoxpropionate, methyl alcohol, ethyl alcohol, propyl alcohol, isopropyl alcohol, butyl alcohol, ethylene glycol, propylene glycol, ethylene glycol monomethyl ether, ethylene glycol monoethyl ether, ethylene glycol monopropyl ether, ethylene glycol monobutyl glycol, diethylene glycol monomethyl ether, diethylene glycol monoethyl ether, diethylene glycol monobutyl ether, propylene glycol monomethyl ether, diethylene glycol monobutyl ether acetate, diethylene glycol monoethyl ether acetate, ethylene glycol monobutyl ether acetate, propylene glycol monomethyl ether acetate, methylene chloride, chloroform, and mixtures thereof.

Also, further suitable solvents can be of the ethylenically unsaturated type that, in addition to dissolving the modified cellulose ester, can react with the modified cellulose ester upon exposure to UV radiation in the presence of a photoinitiator. Specific examples include, but are not limited to: methacrylic acid, acrylic acid, ethyl (meth)acrylate, methyl (meth)acrylate, hydroxyethyl (meth)acrylate, diethylene glycol diacrylate, trimethylolpropane triacrylate, 1,6 hexanediol di(meth)acrylate, neopentyl glycol di(meth)acrylate, N-vinyl pyrrolidone, and mixtures thereof.

The amount of suitable solvent in the solvent-based coating compositions of the present invention is that amount sufficient to solubilize the modified cellulose ester. Typically, this amount of solvent is about 60 to about 90 wt. % of total coating composition, preferably about 65 to about 75 wt. %. Mixtures of solvents can be used in the coatings (and processes) of the present invention.

In the water-dispersed coating compositions of the present invention the suitable co-solvent must be one that is water-miscible and that will solubilize the modified cellulose ester. Typical examples include but are not limited to acetone, 2-butanone, methanol, ethanol, isopropyl alcohol, ethylene glycol monomethyl ether, ethylene glycol monoethyl ether, ethylene glycol monopropyl ether, and ethylene glycol monobutyl ether, ethylene glycol, and propylene glycol. Typical examples of water-soluble ethylenically unsaturated solvents include but are not limited to: methacrylic acid, acrylic acid, N-vinyl pyrrolidone, 2-ethoxyethyl(meth) acrylate, polyethylene glycol dimethacrylate, polypropylene glycol mono(meth)acrylate, and mixtures thereof.

Dispersion in water of those modified cellulose esters containing pendant carboxyl groups requires about 25 to about 100% neutralization of the pendant carboxylate groups with an aliphatic amine. Typical aliphatic amines include but are not limited to 2-amino-2 methyl-1-propanol, piperidine,4-ethylmorpholine, diethanolamine, triethanolamine, ethanolamine, tributylamine, dibutylamine, and ammonia.

The amount of suitable aqueous organic solvent (i.e. organic solvent and water) in the dispersed coating compositions of the present invention is about 50 to about 90 wt. %, preferably about 75 to about 90 wt. % of the total coating composition.

In a preferred embodiment, the maleate has been further reacted with: an aliphatic amine to such an extent as to neutralize approximately 25 to 100% of said maleate moieties; solvent (d), a mixture of a water-miscible solvent and water; and one or more water soluble crosslinking agents, modifying resins, and photoinitiators.

The coating compositions of the present invention contain a photoinitiator. The amount of photoinitiator is typically about 2 to about 7 wt. % based on the weight of the non-volatile, ethylenically unsaturated content of the coating composition; preferably about 3 to about 5 wt. %. The photoinitiator can be any photoinitiator known to one skilled in the art. Examples of photoinitiators include, but are not limited to, benzoin and benzoin ethers such as ESACURE BO, EB1, EB3, and EB4 from Fratelli Lamberti; VICURE 10 and 30 from Stauffer; benzil ketals such as IRGACURE 651 from Ciba Geigy, UVATONE 8302 by Upjohn; alpha, alpha-dialkoxyacetophenone derivatives such as DEAP and UVATONE 8301 from Upjohn; alpha-hydroxyalkylphenones such as IRGACURE 184 from Ciba Geigy; DAROCUR 116, 1173, and 2959 by Merck; mixtures of benzophenone and tertiary amines.

Further details regarding such photoinitiators and curing procedures can be found in U.S. Pat. No. 5,109,097, incorporated herein by reference.

A preferred composition of the invention comprises between about 5 weight % to about 95 weight % of said modified cellulose ester;

between about 2 weight % to about 7 weight % of said photoinitiator;

between about 0.1 weight % to about 90 weight % of a copolymerizable ethylenically unsaturated reactant;

between about 0 weight % to about 90 weight % of a solvent;

between about 0 weight % to about 5 weight % of a pigment;

between about 0 weight % to about 10 weight % of a modifying resin; and between about 0 weight % to about 25 weight % of a plasticizer, based on the weight % of the total composition equalling 100 weight %.

The composition of the invention comprises an ethylenically unsaturated crosslinking agent contains moieties capable of engaging in free radical polymerization, such moieties chosen from the group consisting of: ethylene, dienes, styrene, vinyl esters, acrylic esters, methacrylic esters, and acrylonitrile.

As a further aspect of the present invention there is provided a curable composition as described above, further comprising one or more modifying resins; leveling, rheology, and flow control agents such as silicones, fluorocarbons or cellulosics; flatting agents; pigment wetting and dispersing agents; surfactants; ultraviolet (UV) absorbers; UV light stabilizers; tinting pigments; defoaming and antifoaming agents; anti-settling, anti-sag and bodying agents; anti-skinning agents; anti-flooding and anti-floating agents; fungicides and mildewcides; corrosion inhibitors; thickening agents; or coalescing agents.

Modifying resins are utilized in the composition with ethylenically unsaturated esters to form cross-linking structures that are not as stable as three-dimensional structures utilizing reactive resins, solvents, and ethylenically unsaturated esters, as explained in U.S. Pat. No. 4,839,230, which is incorporated by reference herein. The addition of modifying resins allows the coating as applied to be removed without excessive rubbing with a solvent, unlike prior UV-curable permanent coatings for wood finishing products.

Typical modifying resins include homopolymers and copolymers of (meth)acrylic acid; alkyl esters of (meth) acrylic acid such as allyl, methyl, ethyl, n-propyl, isopropyl, butyl, tetrahydrofurfuryl, cyclohexyl, isobornyl, n-hexyl, n-octyl, isooctyl, 2-ethylhexyl, lauryl, stearyl, benzyl; (meth)acrylated urethane, epoxy, and polyester resins, silicone acrylates, cellulose esters such as cellulose acetate butyrates, cellulose acetate propionates, nitrocellulose, cellulose ethers such as methyl cellulose, ethyl cellulose, hydroxypropyl cellulose, and hydroxypropyl methyl cellulose.

Typical plasticizers include alkyl esters of phthalic acid such as dimethyl phthalate, diethyl phthalate, dipropyl phthalate, dibutyl phthalate, and dioctyl phthalate; citrate esters such as triethyl citrate and tributyl citrate; triacetin and tripropionin; and glyerol monoesters such as Eastman 18-04, 18-07, 18-99 from Eastman Chemical Company.

Any of the compositions of the invention can additionally comprise 0.001 to 50 weight per cent, based on the total weight of the composition, of at least one additional additive selected from a non-polymeric plasticizer, a thermal stabilizer, an antioxidant, a pro-oxidant, an acid scavenger, an ultraviolet light stabilizer, a promoter of photodegradation, inorganics, and colorants. Typical non-polymeric platicizers include dioctyl adipate, phosphates, and diethyl phthalate. Representative inorganics include talc, $TiO_2$, $CaCO_3$, $NH_4Cl$, and silica. Colorants can be monomeric, oligomeric, and, of course, polymeric. Preferred polymeric colorants are aliphatic polyesters, aliphatic-aromatic copolyesters, or aromatic polyesters in which the color producing monomer, i.e., a dye, is covalently incorporated into the polymer. Such representative polymeric colorants are described by Weaver et al. in U.S. Pat. Nos. 4,892,922, 4,892,923, 4,882,412, 4,845,188, 4,826,903, and 4,749,773 and are incorporated herein by reference in their entirety. These polymeric dyes are represented by poly (tetramethylene terephthalate) containing 10% 1,5-bis(O-carboxyanilino) anthraquinone.

Specific examples of additional additives can be found in *Raw Materials Index,* published by the National Paint & Coatings Association, 1500 Rhode Island Avenue, N.W., Washington, D.C. 20005.

The curing of the modified cellulose ester compositions of the present invention can be carried out in the liquid or solid state (i.e., as a dry film).

Depending upon the thickness of the coating (film), product formulation, photoinitiator type, radiation flux, and source of radiation, exposure times to ultraviolet radiation for about 0.5 second to about 30 minutes are typically required for curing. Curing can also occur even in the sunshine.

The coatings of the compositions of the present invention typically have a solvent resistance of at least 200 double rubs using ASTM Procedure D-3732; preferably a solvent resistance of at least 100 double rubs. Such coatings also typically have a pencil hardness of greater than or equal to F using ASTM Procedure D-3363; preferably a pencil hardness of greater than or equal to H.

A general formulation for UV-curable fingernail polishes containing modified cellulose esters of the present invention is as follows:

| | |
|---|---|
| 5–95 weight % | modified cellulose ester as the major film former |
| 0–90 weight % | copolymerizable reactants (monomer, oligomer, or prepolymer) |
| 0–10 weight % | modifying resin |
| 0–25 weight % | plasticizer |
| 0–5 weight % | pigment |
| 2–7 weight % | photoinitiator |
| 0–90 weight % | solvents |

A specific formulation for a UV-curable fingernail polish based on a modified cellulose ester of the present invention is the following:

25 parts modified cellulose ester (major film former)

12 parts ethyl acetate 24 parts butyl acetate 8 parts acrylated urethane resin (preferably EBECRYL 220 from Radcure Industries)

22 parts tripropyleneglycol diacrylate 5 parts N-vinyl pyrrolidone 4 parts photoinitiator (preferably IRGACURE 184 from Ciba Geigy)

Physical mixing of the components of the composition of the invention can be accomplished in a number of ways such as mixing the components in the appropriate solvent (d).

The process of the invention is typically carried out at a temperature of 15° C. to 75° C. The process is particularly useful with all of the compositions described herein.

The article useful in the invention comprises a substrate which includes, but is not limited to, human or animal nails, wood, metal, leather or concrete.

The article of the invention is useful with all of the coating compositions of the invention.

The following examples are put forth so as to provide those of ordinary skill in the art with a complete disclosure and description of how the compounds claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in °C. or is at room temperature and pressure is at or near atmospheric.

Properties of Cellulose Esters Used in the Examples

| Type | Viscosity Poise | Sec | Acetyl[c] % | Butyryl % | Propionyl % | Combined Acetic Acid % | Hydroxyl % | Melting Range °C. | $T_g$ °C. |
|---|---|---|---|---|---|---|---|---|---|
| Cellulose Acetate Propionate | | | | | | | | | |
| CAP 504-0.2 | 0.20 | 0.76 | 0.6 | | 42.5 | | 5.0 | 188–210 | 159 |
| CAP 482-0.5 | 0.40 | 1.52 | 2.5 | | 45.0 | | 2.6 | 188–210 | 142 |
| Cellulose Acetate | | | | | | | | | |
| CA 398-3 | 3.00 | 11.40 | 39.8 | | | 55.5 | 3.5 | 230–250 | 180 |
| Cellulose Acetate Butyrate | | | | | | | | | |
| CAB 381-0.1 | 0.10 | 0.38 | 13.5 | 38.0 | | | 1.3 | 155–165 | 123 |
| CAB 551-0.01 | 0.01 | 0.038 | 2.0 | 53.0 | | | 1.5 | 127–142 | 85 |
| CAB 553-0.4 | 0.30 | 1.14 | 2.0 | 46.0 | | | 4.8 | 150–160 | 136 |

EXAMPLE 1

Preparation of Cellulose Acetate Propionate Maleate (CAP 504-maleate), Sample 4

In a 5-gallon sigma blade mixer are placed 7300 g reagent grade acetic acid and 2500 g of cellulose acetate propionate resin, CAP 504-0.2, commercially available from Eastman Chemical Company, Kingsport, Tenn. The reaction mixture is heated to 65° C., and agitated until all the cellulose ester dissolves. Then 1250 g of maleic anhydride is added and agitated at 65° C. until a clear solution is obtained, after which 1250 g of anhydrous sodium acetate is added. The reaction mixture is heated at 75° C. for three hours and then cooled to 50° C., where upon it is drowned into 9000 g of water with high speed agitation to precipitate the modified cellulose ester product. The precipitated cellulose ester is collected by filtration and then washed with 15,000 g of water. The water-wet modified cellulose ester product is then dried in a vacuum oven at 60° C. to a moisture content of less than 2%. Analysis by nuclear magnetic resonance (NMR) showed the degree of substitution per glucose ring for acetate, propionate and maleate to be 0.40, 2.09 and 0.39, respectively.

EXAMPLE 2

Preparation of Cellulose Acetate Butyrate Maleate (CAB 553-0.4 maleate), Sample 6

In a 5-gallon sigma blade mixture are placed 7300 g reagent grade acetic acid and 2500 g of CAB 553-0.4, commercially available from Eastman Chemical Company, Kingsport, Tenn. (cellulose acetate butyryl content of 46 weight percent, an acetyl content of 2 weight percent, and a hydroxyl content of 4.8 weight percent). The reaction mixture is heated to 65° C. and agitated until all the cellulose ester dissolves. Then 1250 g of maleic anhydride is added and agitated at 65° C. until a clear solution is obtained, after which 1250 g of anhydrous sodium acetate is added. The reaction mixture is heated at 75° C. for three hours and then cooled to 50° C., where upon it is drowned into 9000 g of water with high speed agitation to precipitate the modified cellulose ester product. The precipitated cellulose ester product is collected by filtration and then washed with 15,000 g of water. The water-wet modified cellulose ester is then dried in a vacuum oven at 60° C. to a moisture content of less than 2%. Analysis by nuclear magnetic resonance showed the degree of substitution (DS) per glucose ring for acetate, butyrate, and maleate to be 0.15, 2.1, and 0.41, respectively.

In similar fashion additional samples of modified cellulose esters with a variety of degree of substitution (DS) of substituents were prepared and are given in Table 1:

TABLE 1

| | Cellulose Ester Maleates (DS) | | | | | |
|---|---|---|---|---|---|---|
| Sample | 1 | 2 | 3 | 4 | 5 | 6 |
| Acetate | 1.82 | 0.22 | 0.22 | 0.40 | 0.20 | 0.15 |
| Propionate | — | 2.20 | 2.10 | 2.09 | 2.05 | — |
| Butyrate | — | — | — | — | — | 2.10 |
| Maleate | 0.32 | 0.10 | 0.25 | 0.39 | 0.46 | 0.41 |
| Hydroxyl | 0.86 | 0.48 | 0.43 | 0.12 | 0.29 | 0.34 |

EXAMPLE 3

Preparation of Cellulose Acetate Propionate Methacrylate (CAP 504 Methacrylate), Sample 7

A clean and dry flask with a condenser, stirrer, and thermometer is charged with 500 grams (g) of substantially water-free acetone and 100 g of dry CAP 504-0.2. After the CAP 504-0.2 has dissolved, 76 g of triethylamine and 0.5 g of hydroquinone monomethyl ether are added. The reaction mixture is heated to reflux where upon 114 g of methacrylic anhydride is added over 30 minutes. The reaction is refluxed for 6 hours and cooled to 25° C. It is drowned into 1 liter of water with high-speed agitation. The near white cellulose ester is filtered, washed with water, and dried at 50° C. in a forced-air oven. Analysis by NMR showed a methacrylate (MA) content of 18.6 mol %, which corresponds, to a degree of substitution per glucose ring (DS) of 0.52.

EXAMPLE 4

Preparation of Cellulose Acetate Propionate Methacrylate Ester Grafted with TMI (CAP 504-0.2 TMI/MA), Sample 11

A solution is made consisting of 100 g of dry CAP 504-0.2 and 500 g of urethane-grade propyl acetate. The solution is brought to reflux and approximately 100 g of propyl acetate is distilled out to azeotropically dry the reaction mixture. The solution is cooled to 60° C. and 0.5 g dibutyltin dilaurate and 33 g TMI (meta-isopropenyl-2,2'-dimethyl benzyl isocyanate, commercially available from Cytec Industries) are added. The reaction is refluxed until the —NCO absorption in the infrared spectrum of the reaction mixture is no longer discernable from the baseline. The reaction mixture is cooled to 25° C. and the following were added: 0.5 g HQMME, 23 g of triethylamine, and 20 g of methacryloyl chloride. The reaction mixture is maintained at 40° to 50° C. for six hours, cooled to 30° C. and drowned into 1 liter of hexane with high-speed agitation. The precipitated product is redissolved in 300 mL of acetone and drowned into 1 liter of water with high-speed agitation. The product is filtered and dried at 50° C. The analysis of the cellulose ester by NMR showed the TMI and methacrylate (MA) having a DS per glucose unit to be 0.59 and 0.30, respectively.

In similar fashion additional samples of modified cellulose esters with a variety of DS of substituents were prepared and are given in Table 2:

TABLE 2

Cellulose Esters Containing Ethylenically Unsaturated Pendant Groups (DS)

| Sample | 7 | 8 | 9 | 10 | 11 | 12 |
|---|---|---|---|---|---|---|
| Acetyl | 0.21 | 0.31 | 0.26 | 0.26 | — | 0.11 |
| Hydroxyl | 0.22 | 0.33 | 0.34 | 0.46 | — | — |
| Propionate | 2.05 | 2.11 | — | — | 2.14 | — |
| Butyrate | — | — | 2.00 | 2.05 | — | 2.06 |
| Methacrylate | 0.52 | — | 0.40 | — | 0.30 | 0.21 |
| Acrylate | — | 0.25 | — | 0.20 | — | — |
| TMI | — | — | — | — | 0.59 | 0.62 |

Coating Compositions of Modified Cellulose Ester Samples

Solutions of modified cellulose esters prepared as described herein before (Samples 1–12) were dissolved in butyl acetate with a concentration of 20% by weight of modified cellulose ester containing 5% by weight of photoinitiator (IRGACURE® 184 by Ciba Geigy) and 10% by weight of EBECRYL® 220, an hexacrylated urethane oligomer as a crosslinking agent.

Coating of Glass Substrates

Samples 1–6 were used to coat glass plates. A glass plate was coated with each of the above formulations using a knife blade. The wet film thickness was about 10 mil. The solvent was evaporated to give a clear non-tacky, dust-free film with a thickness of approximately 1 mil. Prior to exposure to UV radiation, each film was readily soluble in organic solvents.

Film Curing

The dried film on the glass plate was exposed to UV radiation from a 200 watt per inch medium pressure mercury vapor lamp housed in an American Ultraviolet Company instrument using a belt speed of 25+ft. per minute. One to five passes under the lamp resulted in a crosslinked coating with maximum hardness and solvent resistance.

Coating Evaluations

Pencil hardness (ASTM D3363), solvent resistance by the methyl ethyl ketone double-rub test, and solubility in acetone were measured for each film before and after exposure to UV radiation. Data for control resins are also included.

The pencil hardness scale is in order of increasing hardness:

5B 4B 3B 2B B HB F H 2H 3H 4H 5H

The methyl ethyl ketone (MEK) double rub test is carried out by saturating a piece of cheesecloth with methyl ethyl ketone, and with moderate pressure, rubbing the coating back and forth. The number of double rubs is counted until the coating is removed. This test is in accordance with ASTM Procedure D-3732.

The acetone solubility test is carried out by immersing a dry, pre-weighed sample of the film in acetone for 48 hours at 25° C. The film is removed, dried for 16 hours at 60° C. in a forced-air oven, and reweighed. The weight percent of the insoluble film remaining is calculated from the data.

COATING EVALUATIONS
Before Irradiation

| Cellulose Ester Type | Pencil Hardness | Acetone Insolubles Wt. % Film Recovery | MEK Double Rubs |
|---|---|---|---|
| CA 320S (Control)[1] | F | 0 | <10 |
| CAP 504 (Control)[1] | HB | 0 | <10 |
| CAB 553 (Control)[1] | 2B | 0 | <10 |
| Nitrocellulose (RS ½ sec.) | 3B | 0 | <10 |
| CA Maleate (0.32 DS) Sample 1 | F | 0 | <10 |
| CAP Maleate (0.10 DS) Sample 2 | F | 0 | <10 |
| CAP Maleate (0.25 DS) Sample 3 | F | 0 | <10 |
| CAP Maleate (0.39 DS) Sample 4 | F | 0 | <10 |
| CAP Maleate (0.46 DS) Sample 5 | F | 0 | <10 |
| CAB Maleate (0.41 DS) Sample 6 | HB | 0 | <10 |
| CAP Methacrylate (0.52 DS) Sample 7 | B | 0 | <10 |
| CAP Acrylate (0.25 DS) Sample 8 | HB | 0 | <10 |
| CAB Methacrylate (0.40 DS) Sample 9 | B | 0 | <10 |
| CAB Acrylate (0.20 DS) Sample 10 | HB | 0 | <10 |
| CAP TMI (0.59 DS) Methacrylate (0.30 DS) Sample 11 | F | 0 | <10 |
| CAB TMI (0.62 DS) Methacrylate (0.2 DS) Sample 12 | HB | 0 | <10 |

[1]Not formulated

| Cellulose Ester Type | After Irradiation | | |
|---|---|---|---|
| | Pencil Hardness | Acetone Insolubles Wt. % Film Recovery | MEK Double Rubs |
| CA 320S (Control)[1] | F | 0 | <10 |
| CAP 504 (Control)[1] | HB | 0 | <10 |
| CAB 553 (Control)[1] | 2B | 0 | <10 |
| Nitrocellulose (RS ½ sec.)[1] | 3B | 0 | <10 |
| CA Maleate (0.32 DS) Sample 1 | H/2H | 94 | >200 |
| CAP Maleate (0.10 DS) Sample 2 | F | 42 | 98 |
| CAP Maleate (0.25 DS) Sample 3 | H | 90 | >200 |
| CAP Maleate (0.39 DS) Sample 4 | H/2H | 94 | >200 |
| CAP Maleate (0.46 DS) Sample | H | 91 | >200 |
| CAB Maleate (0.41 DS) Sample 6 | H/F | 92 | >200 |
| CAP Methacrylate (0.52 DS) Sample 7 | H/F | 31 | 91 |
| CAP Acrylate (0.25 DS) Sample 8 | F | 43 | 62 |
| CAB Methacrylate (0.40 DS) Sample 9 | F | 48 | 109 |
| CAB Acrylate (0.20 DS) Sample 10 | F | 29 | 41 |
| CAP TMI (0.59 DS) Methacrylate (0.30 DS) Sample 11 | 2H | 82 | >200 |
| CAB TMI (0.62 DS) Methacrylate (0.2 DS) Sample 12 | H | 88 | >200 |

[1]Not formulated

EXAMPLE 5

Formulation and Use of Modified Cellulose Ester in a fingernail polish overcoat

Modified cellulose ester (Sample 3) was used in the following nail formulation:

| Component | Parts by Weight |
|---|---|
| Modified cellulose ester (Sample 3) | 16.4 |
| Butyl acetate | 32.6 |
| Ethyl acetate | 15.5 |
| Tecsol ® C 95 ethyl alcohol[1] | 28.2 |
| Ebecryl ® 6700[2] | 3.6 |
| Ebecryl ® 220[3] | 2.7 |
| Irgacure ® 184[4] | 1.0 |

[1]Available from Eastman Chemical Company
[2]Aromatic urethane diacrylate diluted with 15% of 1,6-hexanediol diacrylate - available from Radcure Specialties
[3]Multifunctional aromatic urethane acrylate containing and acrylated polyol diluent - available from Radcure Specialties
[4]Photoinitiator - available from Ciba Geigy The Brookfield viscosity at 25° C. was 100 cP. The % solids content was 23.7%.

The coating was applied to a glass substrate and the solvent evaporated at ambient temperature to leave a dry tack-free film. The dried film on the glass plate was exposed to UV radiation from a 200 watt per inch medium pressure mercury vapor lamp housed in an American Ultraviolet Company instrument using a belt speed of 25 ft. per minute. Two passes under the lamp resulted in a crosslinked coating with maximum pencil hardness and solvent resistance.

EXAMPLE 6

Dispersion of Modified Cellulose Ester (Sample 3) in Water

Into a container with an agitator are placed 30 g of ethylene glycol monobutyl ether, 10 g of water and 15 g of CAP 504-0.2 maleate (0.45 DS maleate, 2.10 DS propionate, 0.25 DS acetate, with acid no. of 78 mg KOH/g of polymer). The contents are agitated until a clear solution is obtained and then the carboxyl groups are neutralized by adding 1.86 g of 2-amino-2-methyl-1-propanol (AMP). After agitation for 5 minutes, 45 g of water is slowly added with agitation to generate a dispersion suitable for coating applications. Additional water can be added as desired.

The formula below is useful for calculating the amount of amine to add for neutralization to any degree of the carboxylic acid pendent groups.

$$\text{wt of amine} = \frac{(\text{wt. of cellulose ester, g})(\text{acid no. of cell. ester})(\text{mw of amine})}{56,100} \times \frac{(\% \text{ carboxyl neutralization})}{100}$$

The Brookfield viscosity at 25° C. was 1025 cP. The % solids content was 15%.

EXAMPLE 7

Formulation and Use of Water-Dispersed, Modified Cellulose Ester (Sample 3) in Water-Reducible, UV-Curable Coating for Nail Polish The water-dispersed sample of Example 6 was used in the following UV-curable top coat formulation:

| Components | Parts by Weight |
|---|---|
| Example 6 (water-dispersed Sample 3) | 97 |
| Trimethylolpropane ethoxy triacrylate[1] | 2 |
| Irgacure ® 184[2] | 1 |

[1]Radcure Business Unit of UCB Chemicals Corporation
[2]Photoinitiator by Ciba Geigy The Brookfield viscosity at 25° C. was 1050 cP. The % solids content is 18%.

The coating was applied to a glass substrate and the solvent evaporated at ambient temperature to leave a dry tack-free film.

The dried film on the glass was exposed to UV radiation from a 200 watt per inch medium pressure mercury vapor lamp housed in an American Ultraviolet Company instrument using a belt speed of 25 ft. per minute. Two passes under the lamp resulted in a crosslinked coating with maximum pencil hardness and solvent resistance.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A photopolymerizable composition for forming a cosmetic coating for nails of humans and animals, comprising:
   (a) at least one modified cellulose esterification or transesterification;
   (b) a photoinitiator; and
   (c) an ethylenically unsaturated crosslinking reagent or copolymerizable ethylenically unsaturated reactant;
   whereby upon exposure to actinic radiation said photopolymerizable composition polymerizes to form a hard and solvent resistant coating on said nails; and wherein,
   (i) said coating is at least partially soluble in a suitable removing solvent;
   (ii) said modified cellulose esterification or transesterification contains maleate or fumarate pendant groups having terminal carboxyl groups; and
   (iii) the terminal carboxyl group of the maleate/fumarate pendant group is optionally reacted with an aliphatic amine.

2. The composition of claim 1 further comprising a solvent (d) capable of solubilizing (a), (b) and (c).

3. The composition according to claim 1, wherein said composition further comprises:
   between about 5 weight % to about 95 weight % of said modified cellulose ester;
   between about 2 weight % to about 7 weight % of said photoinitiator;
   between about 0.1 weight % to about 90 weight % of a copolymerizable ethylenically unsaturated reactant;
   between about 0 weight % to about 90 weight % of a solvent;
   between about 0 weight % to about 5 weight % of a pigment;
   between about 0 weight % to about 10 weight % of a modifying resin; and
   between about 0 weight % to about 25 weight % of a plasticizer, based on the weight % of the total composition equalling 100 weight %.

4. The composition of claim 1 wherein:
   (iv) said modified cellulose esterification or transesterification comprises $\{C_6H_7O_2(OR^1)_x(OR^2)_y(OR^3)_z\}_r$;

(v) r is 2 to 250
   (vi) $(x+y+z)=3$;
   (vii) x is about 0.1–2.5; y is about 0.0–1.0; and z is about 0.0–1.0;
   (viii) at least one of $R^1$, $R^2$ and $R^3$ is;

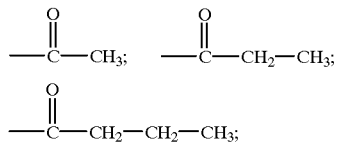

or
   H; and
   (ix) at least one $R^1$, $R^2$ and $R^3$ is independently selected from;

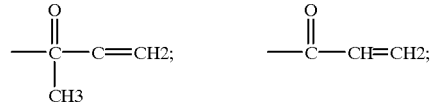

m-isopropenyl-2,2-dimethylbenzyl isocyanate; and
   p-isopropenyl-2,2-dimethylbenzyl isocyanate.

5. The composition according to claim 3 wherein
   said modified cellulose esterification or transesterification comprises $\{C_6H_7O_2(OR^1)_x(OR^2)_y(OR^3)_z\}_r$;

$(x+y+z)=3$;

wherein)
   x is from about 0.1 to 2.5; y is from about 0 to 1.0; z is from about 0 to 1.0; and
   r is 50–250, provided that y and z are not 0 simultaneously.

6. The composition according to claim 5 wherein y is from about 0.1 to 0.4 and z is from about 0.1 to 0.6.

7. The composition according to claim 1, wherein said copolymerizable reactants are selected from the group consisting of: (meth)acrylic acid and its anhydride, crotonic acid, itaconic acid and its anhydride, cyanoacrylic acid and its esters; esters of (meth)acrylic acid such as allyl, methyl, ethyl, n-propyl, isopropyl, butyl, tetrahydrofurfuryl, cyclohexyl, isobornyl, n-hexyl, n-octyl, isooctyl, 2-ethylhexyl, lauryl, stearyl, benzyl, and substituted phenoxyl, behenyl; di(meth)acrylate esters of ethylene and propylene glycols, 1,3-butylene glycols, 1,4-butanediol, diethylene and dipropylene glycols, triethylene and tripropylene glycols, 1,6-hexanediol, neopentyl glycol, polyethylene glycol; and polypropylene glycol, ethoxylated bisphenol, propoxylated neopentyl glycol; tri(meth)acrylate esters of tris-(2-hydroxethyl) isocyanurate, trimethylolpropane, pentaerythritol, glycerol; ethoxylated and propoxylated glycerol; tetra(meth)acrylate esters of pentaerythritol, acrylonitrile, vinyl acetate, vinyl toluene, styrene, N-vinyl pyrrolidinone, alpha-methylstyrene; (meth) acrylated epoxy resins; (meth)acrylated urethanes; (meth) acrylated polyester resins; silicone (meth)acrylates; and mixtures thereof.

8. The composition according to claim 1, wherein said ethylenically unsaturated crosslinking agent contains moieties capable of engaging in free radical polymerization, such moieties chosen from the group consisting of: ethylene, dienes, styrene, vinyl esters, acrylic esters, methacrylic esters, and acrylonitrile.

9. The composition according to claim 3, wherein said copolymerizable reactants further comprise a reactive resin chosen from the group consisting of: epoxy (meth)acrylate, urethane (meth)acrylate, polyester (meth)acrylate, silicon (meth)acrylate, and vinyl acetate.

10. The composition according to claim 2, wherein said solvent (d) is selected from the group consisting of: ketones, alcohols, esters, chlorinated hydrocarbons, glycol ethers, glycol esters, and mixtures thereof.

11. The composition according to claim 2, wherein said solvent (d) comprises a water-miscible co-solvent selected from the group consisting of: acetone, 2-butanone, methanol, ethanol, isopropyl alcohol, ethylene glycol monomethyl ether, ethylene glycol monoethyl ether, ethylene glycol monopropyl ether, and ethylene glycol monobutyl ether, ethylene glycol, propylene glycol, methacrylic acid, acrylic acid, N-vinyl pyrrolidone, 2-ethoxyethyl-(meth)acrylate, polyethylene glycol dimethacrylate, polypropylene glycol mono(meth)acrylate; and mixtures thereof.

12. The composition according to claim 3, wherein said modifying resin is selected from a group consisting of: homopolymers and copolymers of (meth)acrylic acid; alkyl esters of (meth)acrylic acid, (meth)acrylated urethane, epoxy, and polyester resins; silicone acrylates; cellulose esters and mixtures thereof.

13. The composition according to claim 12 wherein said modifying resin is selected from a group consisting of: homopolymers and copolymers of (meth)acrylic acid; alkyl esters of (meth)acrylic acid selected from the group consisting of allyl, methyl, ethyl, n-propyl, isopropyl, butyl, tetrahydrofurfuryl, cyclohexyl, isobornyl, n-hexyl, n-octyl, isooctyl, 2-ethylhexyl, lauryl, stearyl, benzyl; (meth) acrylated urethane, and epoxy; and polyester resins; silicone acrylates; cellulose esters; nitrocellulose; cellulose ethers; and mixtures thereof.

14. The composition according to claim 3, further comprising:
about 25 parts by weight of modified cellulose ester;
about 12 parts by weight of ethyl acetate;
about 24 parts by weight of butyl acetate;
about 8 parts by weight of acrylated urethane resin;
about 22 parts by weight of tripropyleneglycol diacrylate;
about 5 parts by weight of N-vinyl pyrrolidone; and
about 4 parts by weight of a photoinitiator.

15. The composition according to claim 3, wherein said composition further comprises an additive selected from the group consisting of:
dyes;
antifoamants;
opacifiers;
adhesion promoters;
antioxidants;
flow control agents;
flatting agents;
pigment wetting agents;
dispersing agents;
surfactants;
ultraviolet absorbers;
ultraviolet stabilizers;
anti-settling agents;
fungicides and mildewcides;
corrosion inhibitors; and
mixtures thereof.

16. The composition according to claim 5, wherein at least one of $R^1$, $R^2$, and $R^3$ is maleate; x is 0.1 to 2.2, y is 0 and z is 0.1 to 0.46.

17. The composition according to claim 2, wherein said solvent (d) is further comprised of a water miscible co-solvent capable of solubilizing said modified cellulose ester.

18. The composition according to claim 16, wherein R is maleate; x is 1.8–2.2, y is 0.0 and z is 0.25.

19. The coating composition of claim 3, wherein said maleate has been further reacted with: an aliphatic amine to such an extent as to neutralize approximately 25 to 100% of said maleate moieties; solvent (d), a mixture of a water-miscible solvent and water; and one or more water soluble crosslinking agents, modifying resins, and photoinitiators.

20. The coating composition of claim 19, wherein said aliphatic amine is selected from the group consisting of: 2-amino-2-methyl-1-propanol, piperdine, 4-ethylmorpholine, diethanolamine, triethanolamine, ethanolamine, tributylamine, dibutylamine, ammonia, and mixtures thereof.

21. The coating composition according to claim 2 or claim 19, wherein said water-miscible co-solvent is selected from the group consisting of: ketone, alcohol, glycol ether, methacrylic acid and its derivatives, acrylic acid, and N-vinyl pyrrolidone, and mixtures thereof.

22. The coating composition according to claim 3, wherein said modified cellulose ester is further reacted with an aliphatic amine selected from the group consisting of: 2-amino-2 methyl-1-propanol, piperidine, 4-ethylmorpholine, diethanolamine, triethanolamine, ethanolamine, tributylamine, dibutylamine, ammonia, and mixtures thereof.

23. A process for preparing a photopolymerizable composition for forming a cosmetic coating useful for coating nails of humans and animals, comprising:
mixing:
(a) at least one modified cellulose esterification or transesterification;
(b) a photoinitiator; and
(c) a copolymerizable reactant or a copolymerizable ethylenically unsaturated crosslinking reagent;
to form a photopolymerizable composition, wherein upon exposure to actinic radiation said composition polymerizes to form a hard and solvent resistant coating on said nails; and wherein
(i) said coating is at least partially soluble in a suitable removing solvent,
(ii) said modified cellulose esterification or transesterification contains maleate or fumarate pendant groups having terminal carboxyl groups; and
(iii) the terminal carboxyl group of the maleate/fumarate pendant group is optionally reacted with an aliphatic amine.

24. The process according to claim 23 further comprising mixing:
(d) a solvent;
(e) a pigment;
(f) a modifying resin; or
(g) a plasticizer.

25. The process according to claim 23, wherein said step of mixing at least one modified cellulose ester and photoinitiator further comprises:
adding between about 5 weight % to about 95 weight % of said modified cellulose ester;
adding between about 2 weight % to about 7 weight % of said photoinitiator;
adding between about 0.1 weight % to about 90 weight % of a copolymerizable reactants;
adding between about 0 weight % to about 90 weight % of a solvent;
adding between about 0 weight % to about 5 weight % of a pigment;
adding between about 0 weight % to about 10 weight % of a modifying resin; and
adding between about 0 weight % to about 25 weight % of a plasticizer;

wherein the total weight % of the total composition equals 100 weight %.

26. The process of claim 23, carried out at temperature between about 15° C. to 75° C.

27. The process according to claim 23, wherein said step of adding said solvent further comprises adding a compound selected from the group consisting of: acetone, 2-butanone, methanol, ethanol, isopropyl alcohol, ethylene glycol monomethyl ether, ethylene glycol monoethyl ether, ethylene glycol monopropyl ether, ethylene glycol monobutyl ether, ethylene glycol, propylene glycol, methacrylic acid, acrylic acid, N-vinyl pyrrolidone, 2-ethoxyethyl-(meth) acrylate, polyethylene glycol dimethacrylate, polypropylene glycol mono(meth)acrylate; and mixtures thereof.

28. The process according to claim 23, wherein said step of mixing said modified cellulose ester with a copolymerizable reactant further comprises selecting said polymerizable reactant from the group consisting of: (meth)acrylic acid and their anhydrides; crotonic acid; itaconic acid and its anhydride; cyanoacrylic acid and its esters; (meth)acrylic acid esters such as allyl, methyl, ethyl, n-propyl, isopropyl, butyl, tetrahydrofurfuryl, cyclohexyl, isobornyl, n-hexyl, n-octyl, isooctyl, 2-ethlhexyl, lauryl, stearyl, benzyl, and substituted phenoxyl, behenyl; di(meth)acrylate esters of ethylene and propylene glycols, 1,3-butylene glycols, 1,4-butanediol, diethylene and dipropylene glycols, triethylene and tripropylene glycols, 1,6-hexanediol, neopentyl glycol, polyethylene glycol; ethoxylated bisphenol, and propoxylated neopentyl glycol; tri(meth)acrylate esters of tris-(2-hydroxyethyl)isocyanurate, trimethylolpropane, pentaerythritol, glycerol, ethoxylated and propoxylated glycerol; tetra(meth)acrylate esters of pentaerythritol; acrylonitrile, vinyl acetate, vinyl toluene, styrene, N-vinyl pyrrolidinone, and alpha-methylstyrene; (meth)acrylated epoxy resins; (meth)acrylated urethanes; (meth)acrylated polyester resins; silicon (meth)acrylates; and mixtures thereof.

29. The process according to claim 25, wherein said step of adding said modifying resin further comprises adding a compound selected from the group consisting of: homopolymers and copolymers of (meth)acrylic acid; alkyl esters of (meth)acrylic acid such as allyl, methyl, ethyl, n-propyl, isopropyl, butyl, tetrahydrofurfuryl, cyclohexyl, isobornyl, n-hexyl, n-octyl, isooctyl, 2-ethylhexyl, lauryl, stearyl, benzyl; (meth)acrylated urethane, epoxy, and polyester resins, silicone acrylates, cellulose esters such as cellulose acetate butyrates, cellulose acetate propionates; nitrocellulose; cellulose ethers such as methyl cellulose, ethyl cellulose, hydroxypropyl cellulose, and hydroxypropyl methyl cellulose; and mixtures thereof.

30. An article comprising
(1) a human or animal nail substrate, and
(2) a photopolymerized cosmetic coating thereon,
wherein the photopolymerized cosmetic coating comprises a film prepared from a photopolymerizable composition and cured by exposure to actinic radiation; and wherein the photopolymerizable composition comprises:
(a) at least one modified cellulose esterification or trans-esterification;
(b) a photoinitiator; and
(c) an ethylenically unsaturated crosslinking reagent or copolymerizable ethylenically unsaturated reactant; and wherein,
(i) said coating is at least partially soluble in a suitable removing solvent,
(ii) said modified cellulose esterification or transesterification contains maleate or fumarate pendant groups having terminal carboxyl groups; and
(iii) the terminal carboxyl group of the maleate/fumarate pendant group is optionally reacted with an aliphatic amine.

31. The article of claim 30, wherein said coating has a solvent resistance of at least 100 rubs using ASTM Procedure D-3732, and a pencil hardness of greater than or equal to F using ASTM Procedure D3363.

32. The article of claim 31, wherein said coating has a pencil hardness of greater than or equal to H using ASTM Procedure D3363.

33. A process comprising the steps of;
1) providing a photopolymerizable composition
2) coating a human or animal nail with the photopolymerizable composition: and
3) curing the photopolymerizable composition by exposure to actinic radiation, to form a hard and solvent resistant coating on said nail;
wherein the photopolymerizable composition comprises:
(a) at least one modified cellulose esterification or transesterification;
(b) a photoinitiator; and
(c) an ethylenicaly unsaturated crosslinking reagent or copolymerizable ethylenically unsaturated reactant; and wherein;
(i) said coating is at least partially soluble in a suitable removing solvent,
(ii) said modified cellulose esterification or transesterification contains maleate or fumarate pendant groups having terminal carboxyl groups; and
(iii) the terminal carboxyl group of the maleate/fumarate pendant group is optionally reacted with an aliphatic amine.

34. The process of claim 33 wherein:
the photopolymerizable composition additionally comprises:
(d) reactive resin;
(e) a pigment;
(f) a modifying resin;
(g) a plasticizer; or
(h) a solvent.

35. The process of claim 33 wherein:
(iv) said modified cellulose esterification or transesterification comprises

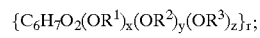

(v) r is 2 to 250;
(vi) (x+y+z)=3;
(vii) x is about 0.1–2.5; y is about 0.1–0.0; and z is about 0.0–1.0;
(viii) at least one of $R^1$, $R^2$ and $R^3$ is

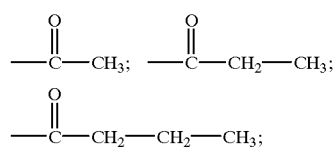

or

H; and (ix) at least one $R^1$, $R^2$ and $R^3$ is independently selected from;

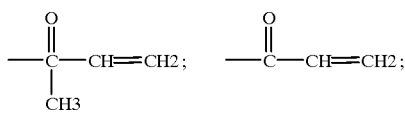

m-isopropenyl-2,2-dimethylbenzyl isocyanate; and
p-isopropenyl-2,2-dimethylbenzyl isocyanate.

36. The process of claim 23 wherein:

(iv) said modified cellulose esterification or transesterification comprises

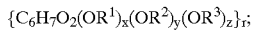

(v) r is 2 to 250;
(vi) (x+y+z)=3;
(vii) x is about 0.1–2.5; y is about 0.0–1.0; and z is about 0.0–1.0;
(viii) at least one of $R^1$, $R^2$ and $R^3$ is;

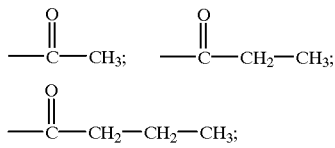

or
H; and (ix) at least one $R^1$, $R^2$ and $R^3$ is independently selected from;

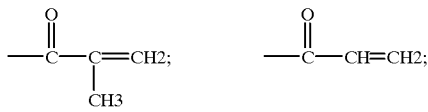

m-isopropenyl-2,2-dimethylbenzyl isocyanate; and
p-isopropenyl-2,2-dimethylbenzyl isocyanate.

37. The process of claim 30 wherein:

(iv) the modified cellulose esterification or transesterification comprises

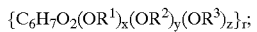

(v) r is 2 to 250;
(vi) (x+y+z)=3;
(vii) x is about 0.1–2.5; y is about 0.1–1.0; and z is about 0.1–1.0;
(viii) at least one of $R^1$, $R^2$ and $R^3$ is;

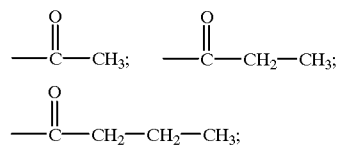

or
H; and (ix) at least one $R^1$, $R^2$ and $R^3$ is independently selected from;

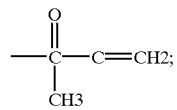

m-isopropenyl-2,2-dimethylbenzyl isocyanate; and
p-isopropenyl-2,2-dimethylbenzyl isocyanate.

38. The composition according to claim 37, wherein r is from 50 to 250.

* * * * *